United States Patent
Crawley et al.

(10) Patent No.: US 7,776,101 B2
(45) Date of Patent: *Aug. 17, 2010

(54) SOFT TISSUE DEFECT REPAIR DEVICE

(75) Inventors: Jerald M. Crawley, Flagstaff, AZ (US); John M. Herman, Elkton, MD (US); William D. Montgomery, Flagstaff, AZ (US); Charles F. White, Camp Verde, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 1405 days.

This patent is subject to a terminal disclaimer.

(21) Appl. No.: 11/015,147

(22) Filed: Dec. 17, 2004

(65) Prior Publication Data
US 2005/0165447 A1    Jul. 28, 2005

Related U.S. Application Data

(63) Continuation-in-part of application No. 10/465,110, filed on Jun. 18, 2003, now Pat. No. 6,991,637.

(51) Int. Cl.
*A61F 2/02* (2006.01)

(52) U.S. Cl. ............ 623/23.72; 623/14.13; 600/37; 606/151

(58) Field of Classification Search ........... 623/14.13, 623/23.72, 23.73, 23.74, 23.75, 23.76; 606/151–156; 600/37
See application file for complete search history.

(56) References Cited

U.S. PATENT DOCUMENTS

| 4,769,038 A | | 9/1988 | Bendavid et al. ............ 623/13 |
| 4,854,316 A | | 8/1989 | Davis ........................ 128/334 |
| 4,891,263 A | * | 1/1990 | Kotliar et al. .............. 442/301 |
| 4,990,158 A | | 2/1991 | Kaplan et al. ................. 623/1 |
| 5,092,884 A | * | 3/1992 | Devereux et al. .......... 623/23.72 |
| 5,098,779 A | | 3/1992 | Kranzler et al. .......... 428/306.6 |
| 5,116,357 A | * | 5/1992 | Eberbach .................... 606/213 |
| 5,147,374 A | * | 9/1992 | Fernandez .................. 606/151 |
| 5,254,133 A | | 10/1993 | Seid ........................... 606/215 |

(Continued)

FOREIGN PATENT DOCUMENTS

GB    2222954    3/1990

(Continued)

OTHER PUBLICATIONS

U.S. Appl. No. 60/405,517, filed Jan. 23, 2002, Gingras.

*Primary Examiner*—Paul Prebilic
(74) *Attorney, Agent, or Firm*—Eric J. Sheets

(57) ABSTRACT

An inguinal hernia repair device in the form of an implantable plug that is affixed at one end to the center region of a sheet of implantable material. The plug takes the form of a plurality of hollow members, arranged so as to be in substantially parallel relationship when implanted into a defect. The hollow members are preferably tubular members and are preferably bundled together by various means, such as bonding or wrapping a band or strand about the plurality of hollow members to maintain them in adjacent and contacting relationship during insertion into a defect. The device is provided with a base member for anchorage made of a composite material having a non-bioabsorable component and a bioabsorbable component.

6 Claims, 9 Drawing Sheets

U.S. PATENT DOCUMENTS

| | | | |
|---|---|---|---|
| 5,258,000 A | 11/1993 | Gianturco | 606/151 |
| 5,356,432 A | 10/1994 | Rutkow et al. | 606/151 |
| 5,425,766 A * | 6/1995 | Bowald | 623/13.18 |
| 5,462,781 A * | 10/1995 | Zukowski | 428/36.1 |
| 5,508,036 A | 4/1996 | Bakker et al. | |
| 5,593,441 A | 1/1997 | Lichtenstein et al. | 623/11 |
| 5,709,713 A * | 1/1998 | Evans et al. | 623/1.53 |
| 5,716,408 A | 2/1998 | Eldridge et al. | 623/11 |
| 5,858,505 A | 1/1999 | Moen et al. | |
| 6,113,641 A * | 9/2000 | Leroy et al. | 623/23.75 |
| 6,165,217 A | 12/2000 | Hayes | 623/11.11 |
| 6,166,286 A | 12/2000 | Trabucco | 623/11 |
| 6,180,848 B1 | 1/2001 | Flament et al. | 623/11 |
| 6,241,768 B1 | 6/2001 | Agarwal et al. | 623/11.11 |
| 6,270,530 B1 | 8/2001 | Eldridge et al. | 623/23.74 |
| 6,309,423 B2 * | 10/2001 | Hayes | 623/23.75 |
| 6,425,924 B1 | 7/2002 | Rousseau | 623/23.64 |
| 6,551,353 B1 * | 4/2003 | Baker et al. | 623/1.42 |
| 6,562,068 B2 * | 5/2003 | Drasler et al. | 623/1.24 |
| 6,755,867 B2 | 6/2004 | Rousseau | 823/23.72 |
| 6,755,868 B2 | 6/2004 | Rousseau | 623/23.72 |
| 6,991,637 B2 * | 1/2006 | Crawley et al. | 606/151 |
| 7,377,929 B2 * | 5/2008 | Crawley et al. | 606/151 |
| 2001/0027347 A1 | 10/2001 | Rousseau | |
| 2003/0181988 A1 | 9/2003 | Rousseau | |
| 2003/0225355 A1 * | 12/2003 | Butler | 602/48 |
| 2009/0240267 A1 * | 9/2009 | Crawley et al. | 606/151 |

FOREIGN PATENT DOCUMENTS

| | | |
|---|---|---|
| WO | 2004/017869 | 3/2004 |
| WO | 2004/112648 | 12/2004 |

\* cited by examiner

SOFT TISSUE DEFECT REPAIR DEVICE

CROSS REFERENCE TO RELATED APPLICATIONS

This application is a continuation-in-part of application Ser. No. 10/465,110, filed Jun. 18, 2003 now U.S. Pat. No. 6,991,637.

FIELD OF THE INVENTION

The present invention relates to the field of soft tissue defect repair devices, and more particularly to the field of inguinal hernia repair devices.

BACKGROUND OF THE INVENTION

The repair of inguinal hernias is one of the most commonly performed surgical procedures. Various prosthetic materials, typically porous to allow for tissue ingrowth, have been provided in a variety of combinations, forms and shapes. Surgical mesh, typically of polypropylene, has been commonly used, in some instances having been rolled up into a cylindrical shape and inserted into the defect as a plug. To reduce the tendency to migrate, these plugs are sometimes affixed at one end to the center of a sheet of material. The sheet is used to overlap the defect and for attachment to the adjacent tissue to reduce the likelihood of migration of the device; see, for example, U.S. Pat. No. 5,116,357 to Eberbach and U.S. Pat. No. 5,147,374 to Fernandez. These sheet-and-plug devices lend themselves to laparoscopic repair as they may be inserted via a trocar wherein, after insertion, the edges of the sheet may be fastened to the tissue adjacent the defect.

Hernia repair plug devices have been refined into a variety of shapes. One such commercially available device is the PerFix® Plug (polypropylene mesh) from C. R. Bard, Inc. (Murray Hill N.J.), described in U.S. Pat. No. 5,356,432 to Rutkow et al. and in revised form by U.S. Pat. No. 5,716,408 to Eldridge et al. This device is in the form of a pleated conical fabric mesh provided with additional mesh filler material within the hollow of the cone; a sheet of material is not attached to the plug. These attributes are said to aid in the insertion of the device into a hernia defect (In the axial direction with regard to the device) and to better enable the device to fill the defect in the radial direction. However, there are reported cases of devices of this type having migrated from the site of the defect. Further, the mesh filler material is often not adequate to provide the necessary axial stiffness and radial compliance to the conical form.

U.S. Pat. No. 6,425,924 to Rousseau teaches two opposing conical mesh shapes fitted together on a common axis and separated by one or more tubular components, also on the common axis, with the apices of the two cones pointed away from each other. The apex of one cone is affixed to the center of a sheet of mesh material.

Various materials have been discussed for use as prosthetic plugs for the repair of inguinal hernias. Polypropylene and polytetrafluoroethylene are commonly discussed. Polypropylene is most often used in the form of a woven or knitted mesh fabric to create the desired shapes. Polytetrafluoroethylene is typically used in its porous, expanded form, usually noted as ePTFE. Other described non-absorbable materials include cotton, linen, silk, polyamide (e.g., nylon 66) and polyethylene terephthalate. Various absorbable materials have also been proposed, including homopolymers and copolymers of glycolide and lactide, caprolactones and trimethylene carbonates. See, for example, U.S. Pat. No. 6,113,641 to Leroy et al., U.S. Pat. No. 6,180,848 to Flament et al., and U.S. Pat. No. 6,241,768 to Agarwhal et al.

U.S. Provisional Patent Application Ser. No. 60/405,517 to Gingras discloses a soft tissue implant used to treat body defects or to remodel tissue. The implant is in the form of a braided or woven material having a variety of shapes. The braided or woven material can be made of non-absorbable or absorbable polymeric material. The Gingras device does not combine absorbable materials with non-absorbable materials, however. An onlay or anchor can be attached to the implant to reduce or eliminate migration of the implant.

An implantable space-filling tissue repair device having an anchoring element made of non-bioabsorbable components in combination with bioabsorbable components would provide different tissue responses to the anchoring element at different times during the healing and/or remodeling process. In addition, the bioabsorbable materials of the anchoring element would alter the mechanical characteristics of the non-bioabsorbable materials of the element. This would allow for more variability in the design and construction of the non-bioabsorbable materials of the anchoring element. Once the bioabsorbable material has disappeared from the anchoring element, the non-bioabsorbable component would remain in place and continue to provide support to the repaired or remodeled tissue.

Accordingly, there remains a need for an implantable medical device having a bioabsorbable and/or non-bioabsorbable space-filling portion and one or more anchoring elements made of non-bioabsorbable materials in combination with bioabsorbable materials. A preferred bioabsorbable material would be a synthetic polymeric material in the form of a self-cohering web.

SUMMARY OF THE INVENTION

The present invention is directed to an inguinal hernia repair device in the form of an implantable plug that is affixed at one end to the center region of a sheet of implantable material, with the length of the plug component oriented to be substantially perpendicular to the sheet. The implantable sheet material is substantially planar and serves as a base member for the implantable plug portion of the present invention to participate in anchoring the invention at an implantation site. Accordingly, the implantable sheet material is referred to herein either as an "anchoring element," or a "base member."

In this invention, the base member is made of one or more non-bioabsorbable components in combination with one or more bioabsorbable components. The non-bioabsorbable component is preferably polymeric. Suitable non-bioabsorbable polymeric materials include biocompatible alkenes, such as polyethylene and polypropylene, and biocompatible fluoropolymers. Preferred non-bioabsorbable polymeric materials are configured with a multiplicity of pores, voids, holes, or other spaces through and/or throughout the material. The spaces can be of various sizes and are either isolated or interconnected in the polymeric material. In preferred embodiments, these spaces in the non-bioabsorbable component serve as repositories for the bioabsorbable component. In many preferred embodiments, the bioabsorbable component is selectively placed within spaces and/or on surfaces of the non-bioabsorbable component. Selectively placing the bioabsorbable component on the non-bioabsorbable component permits the tissue response and the mechanical properties of the base member to be altered, or adjusted, for a particular medical procedure or physiological requirement.

The plug portion of the present invention takes the form of a plurality of hollow, or substantially hollow, members, arranged so as to be in substantially parallel relationship when implanted into a defect. The hollow members are preferably bundled together by various means, such as bonding or wrapping a band or strand about the plurality of hollow members to maintain them in adjacent and contacting relationship during insertion into a defect.

The hollow members are preferably tubular in shape and can be made of non-bioabsorbable materials and/or bioabsorbable materials. Preferably, the hollow members are made of a non-woven bioabsorbable material. More preferably, the non-woven bioabsorbable material is in the form of a web. Most preferably, the non-woven bioabsorbable web is a self-cohering web. The use of a plurality of hollow members provides for good axial stiffness, beneficial during insertion into the defect, in combination with good radial compliance due to the transverse compressibility of the relatively thin-walled tubes. Preferably, a plurality of discrete, individual hollow members are used, with at least one end of each hollow member remaining open to allow rapid access for body fluids and living cells. The open end of the hollow members is located at the end of the plug opposite the end that is affixed to the sheet of implantable material. As noted above, the plurality of hollow members may be affixed at one end to the center region of a sheet of implantable material that serves to anchor the device in the preperitoneal space and ensure proper placement and retention of the plug.

In a preferred embodiment, the hollow members are about twice the desired length of the plug component. Each hollow member is folded in half at the midpoint of its length, with all hollow members attached at the fold to the sheet component. The plurality of folded hollow members is then bundled together as described above.

The hollow members and the sheet component may be made from any suitable implantable materials including both bioabsorbable and non-bioabsorbable materials. The entire device may be made to be non-bioabsorbable, or alternatively the entire device may be made to be absorbable. The plug may be made to be absorbable and affixed to a non-bioabsorbable sheet, or vice versa. Bioabsorbable materials are preferred, particularly for the plug component, in that they are anticipated to elicit an inflammatory tissue response that may result in more rapid healing. The most preferred sheet materials have one or more non-bioabsorbable components placed within, or between, bioabsorbable components.

If desired, the length of the substantially hollow members may be reduced by trimming with a cutting tool.

A preferred bioabsorbable material for the hollow member components and the bioabsorbable components of the base member material is a copolymer of poly(glycolide:trimethylene carbonate). The copolymer's polyglycolide component is commonly abbreviated as PGA for poly(glycolic acid), the chemical byproduct to which it degrades after hydrolysis. The poly(trimethylene carbonate) component is commonly abbreviated as TMC, with the copolymer itself typically referred to as PGA:TMC accompanied with relative percentage composition by weight. The preferred PGA:TMC copolymer embodiment is in the form of a non-woven self-cohering web as taught by Hayes in U.S. Pat. Nos. 6,165,217 and 6,309,423, both of which are incorporated herein by reference.

Preferably, the non-bioabsorbable component is made of a fluoropolymer. More preferably, the fluoropolymer is polytetrafluoroethylene. Most preferably, the polytetrafluoroethylene is porous, expanded, polytetrafluoroethylene (ePTFE). Other polymeric materials suitable for use in making non-bioabsorbable portions of the device include, but are not limited to, polyethylene and polypropylene Either or both of the sheet component and the space-filling plug component may optionally be treated (e.g., impregnated or coated) with any of various bioactive agents, including but not limited to antimicrobials, antibiotics, palliatives, and pharmacological, biochemical, and genetic therapeutics. This is possible regardless of whether the material used for the treated component is bioabsorbable or non-bioabsorbable.

Accordingly, one embodiment of the present invention is an implantable hernia repair device comprising a plurality of substantially hollow members, wherein each substantially hollow member has two ends and at least one of said ends is open, wherein each substantially hollow member is made of a bioabsorbable polymeric material in the form of a self-cohering web, and wherein said plurality of substantially hollow members is attached to a substantially planar base member in the form of a composite made of a non-bioabsorbable polymeric material placed within a bioabsorbable polymeric material in the form of a self-cohering web.

Another embodiment of the present invention is an implantable hernia repair device comprising a plurality of substantially hollow members, wherein each substantially hollow member has two ends and at least one of said ends is open, wherein each substantially hollow member is made of a bioabsorbable polymeric material in the form of a self-cohering web, and wherein said plurality of substantially hollow members is attached to a substantially planar base member in the form of a composite made of a non-bioabsorbable polymeric material placed between at least two layers of a bioabsorbable polymeric material in the form of a self-cohering web.

DETAILED DESCRIPTION OF THE INVENTION

Figure 1:
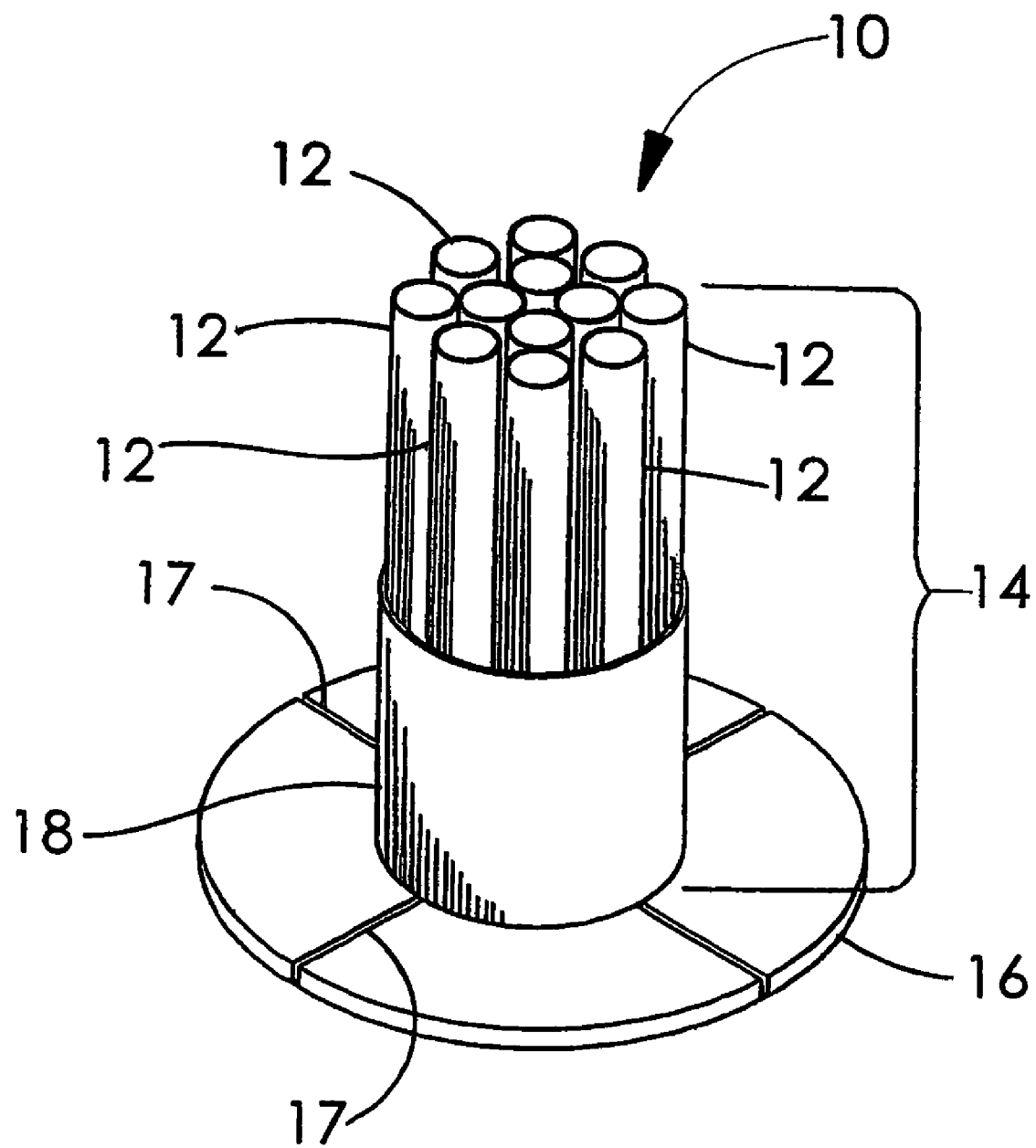
FIG. 1 is a perspective view of a hernia repair device of the present invention.

FIG. 1 is a perspective view of a hernia repair device 10 of the present invention, wherein a plurality of hollow, or substantially hollow, members 12 are provided in substantially parallel relationship, creating plug 14. Preferably, hollow members 12 are tubular as shown in this embodiment. Optionally and preferably, one end of plug 14 is affixed to the approximate center of a sheet 16 of composite implantable material. Sheet 16 may optionally be provided with one or more slits 17 as desired to increase flexibility of sheet 16 and to better enable it to be folded as necessary for insertion.

Though preferred, hollow members 12 are not required to be tubular. Consequently, each hollow member 12 is not required to have either a round or continuous (uninterrupted) circumference. The hollow members may, for example, be tubes provided with a slit along all or a portion of their length in order to further increase their radial or transverse compressibility. While round transverse cross sections are preferred, other shapes such as square, rectangular, hexagonal, elliptical, etc. may be used. The transverse cross sectional shapes of the hollow members making up an individual plug may all be the same, or two or more different transverse cross sectional shapes may be used in combination to make up a single plug.

Hollow members 12 are preferably provided in a bundle that results in their being substantially parallel to each other when inserted. By "substantially parallel" in this context is meant that the hollow members vary only about +/−20 degrees, and more preferably only about +/−10 degrees, from perfectly parallel. The hollow members may be maintained in a bundled relationship by various bundling means, such as bonding together outer surfaces of adjacent hollow members or wrapping a band 18 or strand about the plurality of hollow members 12 to maintain them in adjacent and contacting relationship during insertion into a defect. The bundled relationship may also result from the means used to affix the individual hollow members 12 to a sheet 16.

For embodiments wherein plug 14 is fabricated from a bioabsorbable material, band 18 or any other suitable bundling means may be made from an a material that bioabsorbs, bioresorbs, or dissolves faster than the material of plug 14. As such, band 18 (or other bundling means) can be expected to bioabsorb, bioresorb, or dissolve before the plug and will release the hollow members to allow them to better conform to the shape of the defect into which they were inserted when contained by the bundling means.

Hollow, or substantially hollow, members 12 have opposing ends wherein one end of each of the plurality of hollow members remains open, thereby allowing access of body fluids and cells into the luminal space of each hollow member. This is anticipated to increase the rate of tissue attachment and healing, particularly if the hollow members 12 comprise a bioabsorbable material. The end of each hollow member 12 opposing the open end may be affixed to the central region of sheet 16.

Figure 1A:
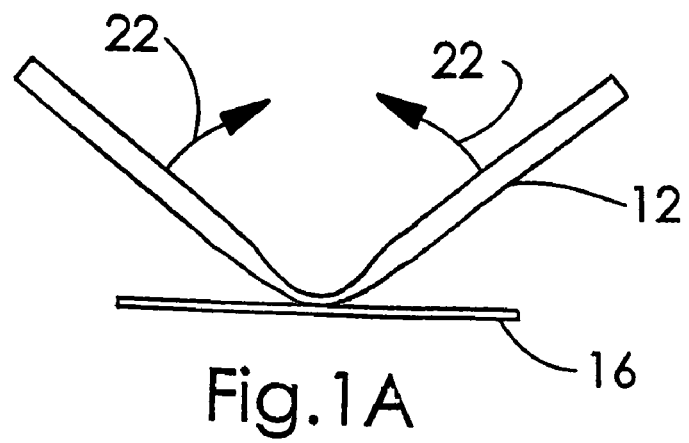
FIG. 1A is a side view of a method of making the device of FIG. 1.

Alternatively, as shown by FIG. 1A, each hollow member 12 may be of a length that is about twice the length of plug 14, wherein individual hollow members 12 are folded in half transversely (indicated by arrows 22) at about the midpoint of their length, and attached at the fold to sheet 16.

Attachment of hollow members 12 to sheet 16 may be accomplished in a variety of manners, depending on the configuration of hollow members 12 and the materials selected for the hollow members 12 and sheet 16. The various affixing means include the use of adhesives suitable for the chosen materials, various mechanical attachment means such as sewing with suitable materials (e.g., suture materials), or welding means such as the appropriate application of heat, solvent welding and/or by ultrasonic welding.

Figure 1B:
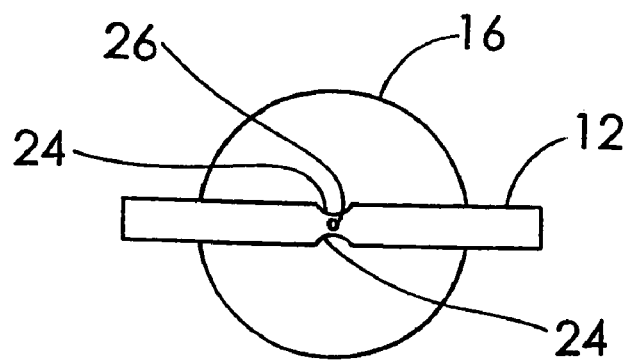
FIGS. 1B and 1C are top views further illustrating the method of FIG. 1A.
Figure 1C:
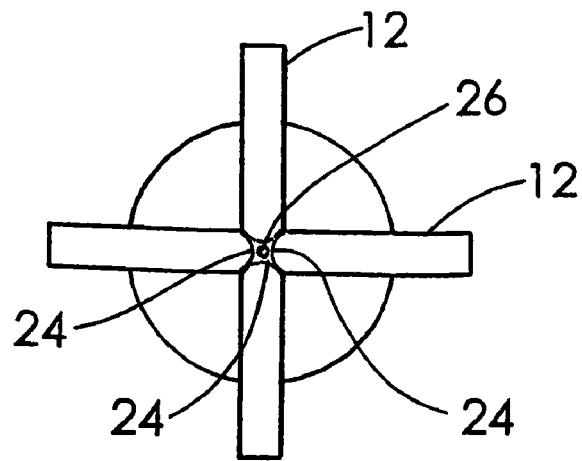

A preferred method of making the embodiment with folded hollow members is shown in the top views of FIGS. 1B and 1C. FIG. 1B shows how a hollow member 12 may be provided with opposing notches 24 along its sides to better enable additional hollow members to be stacked at the same attachment point as further shown in FIG. 1C. Notches 24 reduce the interference resulting from multiple hollow members 12 being attached at different angles at the common location. It is apparent that a plurality of hollow members 12 may be attached at the common location in this manner. The hollow members may be further provided with a hole 26 at the center of the transverse fold line to accommodate a temporary locating pin (not shown for clarity; for use only during fabrication until the assembly is complete). Conversely, such a locating pin might be made from a suitable bioabsorbable material and remain in place as a part of the device construction.

Figure 2:
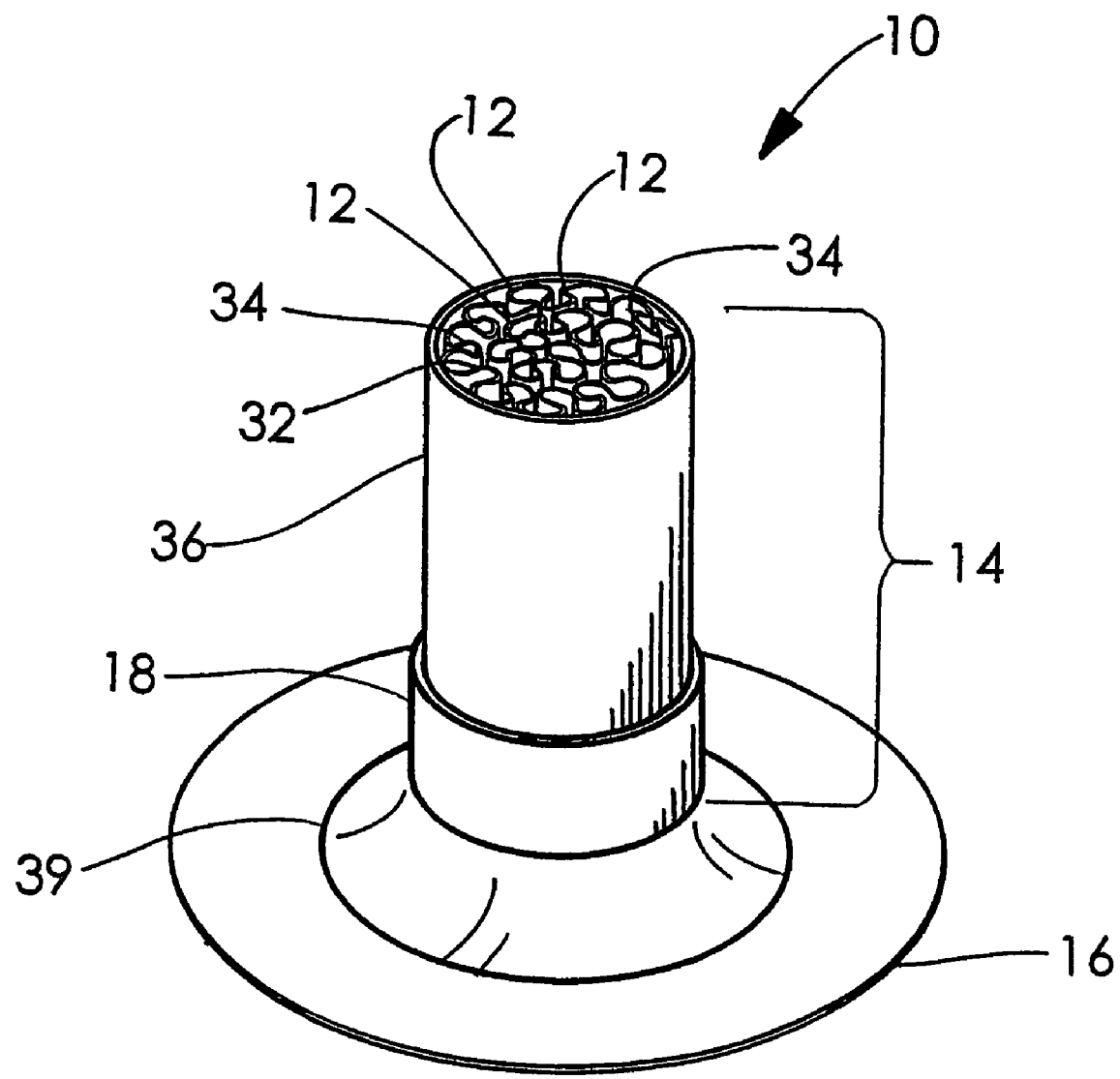
FIG. 2 is a perspective view of an alternative hernia repair device of the present invention wherein a corrugated sheet is rolled to create the plug component.

FIG. 2 is a perspective view of an alternative hernia repair plug of the present invention describing an embodiment wherein the hollow members 12 are in the form of a corrugated material 32 that is rolled up or otherwise bundled to form plug 14. The corrugated material 32 may be rolled up to create the plug 14 or simply folded and bundled by wrapping with a band 18 or my other means described previously. Plug 14 is affixed to sheet 16 as described previously. For any of the embodiments described herein, the resulting juncture of plug 14 and sheet 16 may be optionally reinforced by a fillet component 39. Fillet 39 is simply a disc of suitable material fitted around the base of plug 14 with enough interference to cause it to fit tightly around the base of plug 14. Fillet 39 may be joined to sheet 16 and plug 14 by various affixing methods described previously. Alternatively, sheet 16, fillet 39 and band 18 may be formed of a single piece.

Figure 2A:
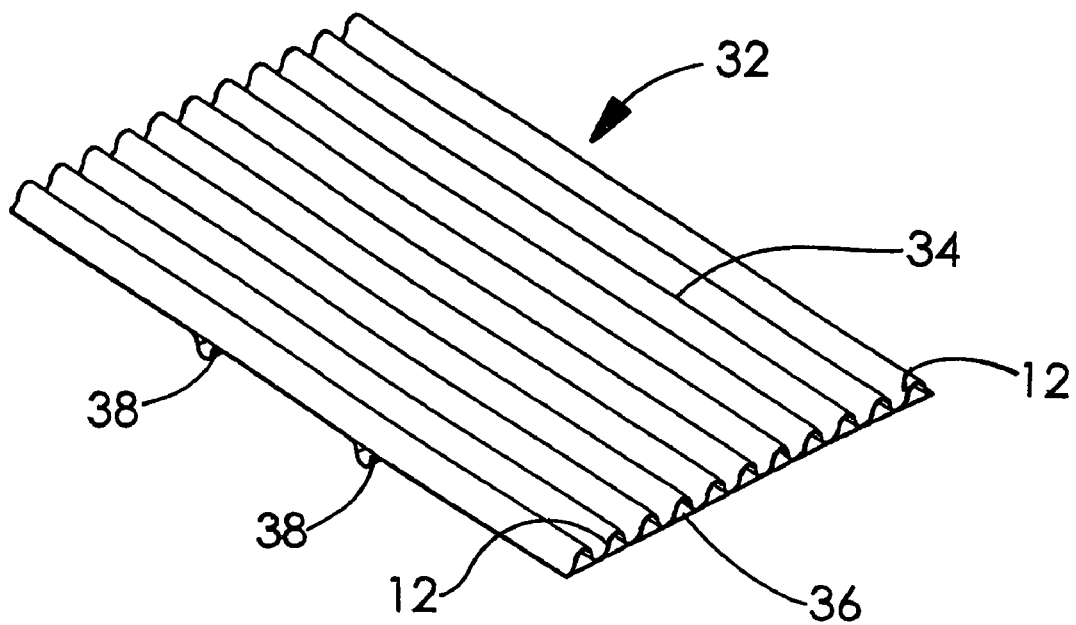
FIGS. 2A and 2B are upper and lower perspective views of the corrugated sheet prior to rolling up to create the plug.
Figure 2B:
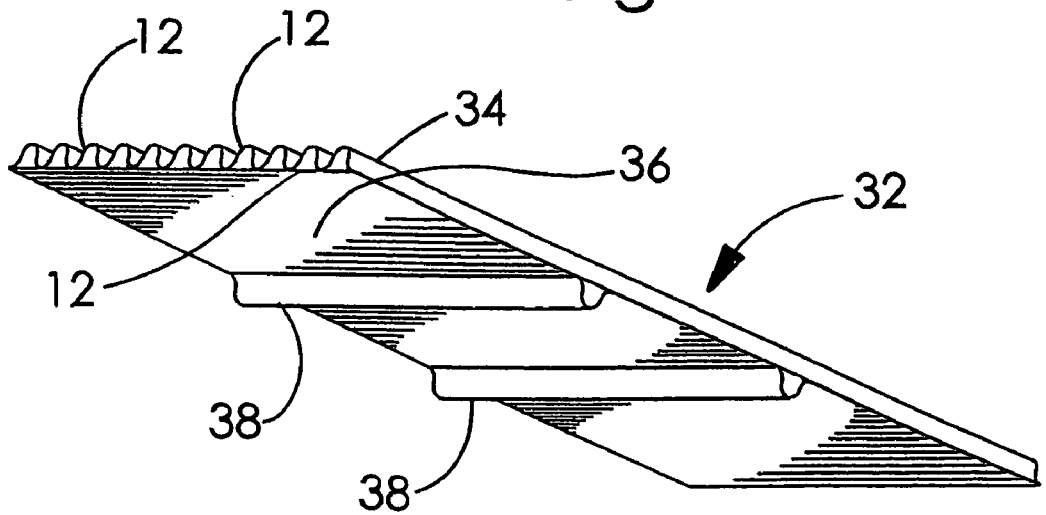

FIGS. 2A and 2B show respectively upper and lower perspective views of a corrugated sheet material suitable for rolling or otherwise bundling to create plug 14. The corrugated sheet 32 comprises an upper layer 34 that is corrugated and affixed to a planar lower layer 36 by any suitable means. The corrugations result in a plurality of hollow members 12. Rolling of the corrugated sheet 32 to create plug component 14 is accomplished by rolling in a direction transverse to the length of the corrugations. As shown by FIG. 2, this results in the corrugations that provide the plurality of hollow members 12 extending along the length of the cylindrical plug 14, parallel to the longitudinal center line of the plug 14. The ends of the corrugations, opposite the end of the plug that is subsequently affixed to sheet 16, remain open. The corrugated sheet material 32 may be made from any desired bioabsorbable or non-bioabsorbable material. These corrugated sheets are anticipated to have other implantable applications in addition to use as the plug component of the hernia repair device described herein. For example, the corrugated sheet material 32 may be useful in planar form for the repair of various tissue defects where a somewhat flexible, but "reinforced" sheet is desired. They may also have utility when rolled up to create a cylindrical shape appropriate for other applications. The hollow members resulting from the corrugated construction may be beneficial for various implantable applications.

Figure 3:
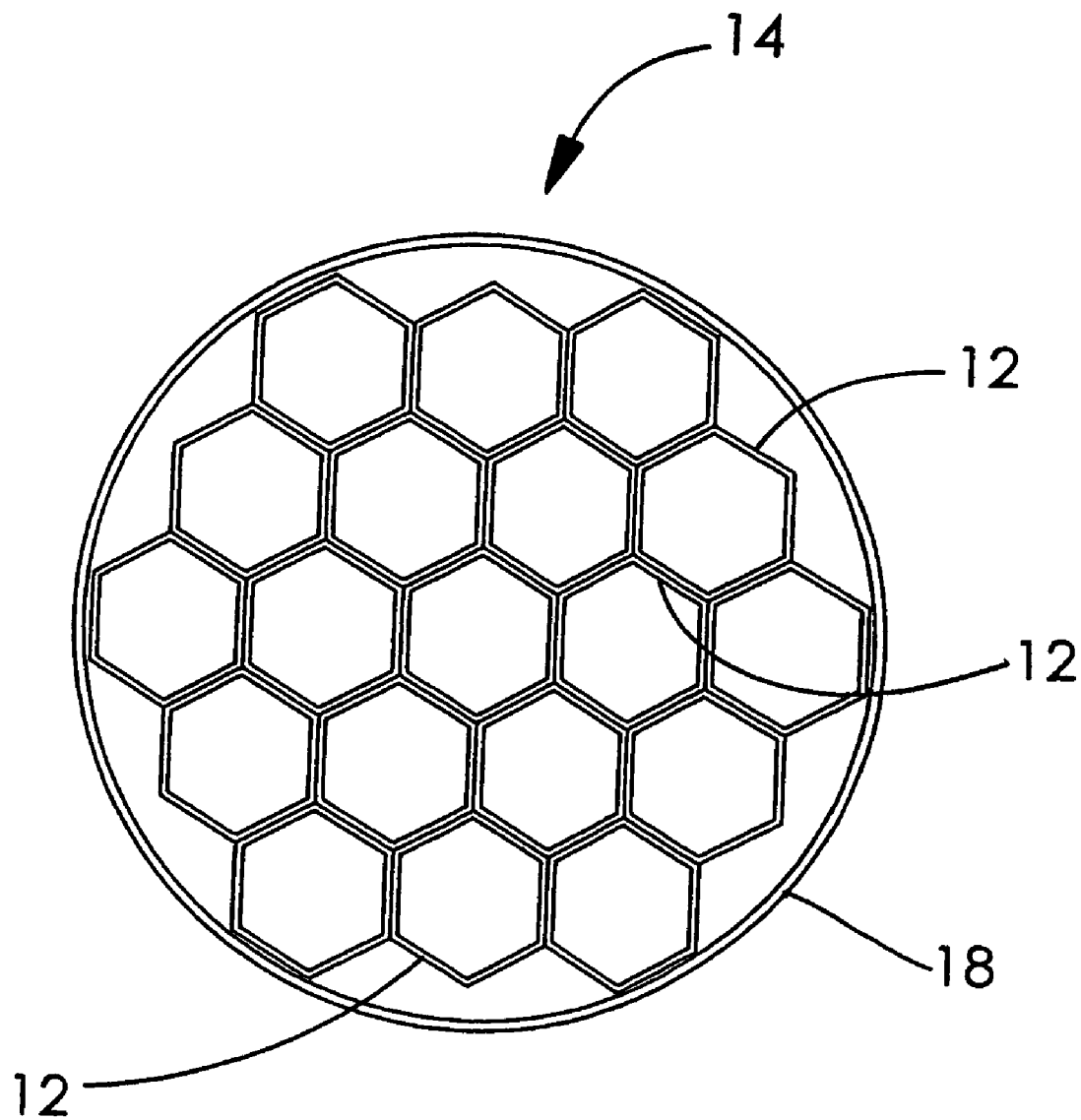
FIG. 3 is an end view of an embodiment wherein the hollow members have hexagonal transverse cross sections.

Optionally, as shown by FIGS. 2A and 2B, corrugated sheet material 32 may be provided with one or more transverse corrugations 38 on the lower surface of planar lower layer 36. When the corrugated sheet material is rolled up to create plug 14 of FIG. 2, these corrugations 38 become barbs or anchoring features extending circumferentially around the outer surface of plug 14, as will be further described. Corrugations 38 must be adequately flexible or distortable to allow the corrugated sheet 32 to be rolled up in the direction of their length. If desired, corrugations 38 may be cut transversely at intervals along their length to better enable the corrugated sheet 32 to be rolled up FIG. 3 shows a top view of plug 14 wherein the hollow members 12 have hexagonal transverse cross sections. Plug 14 may result from bundling a plurality of individual hollow members 12 or alternatively the members may be provided by extrusion of a honeycomb form wherein adjacent hollow members 12 share common walls. It is apparent that hollow members 12 may be provided in a variety of cross sectional shapes.

Figure 4:
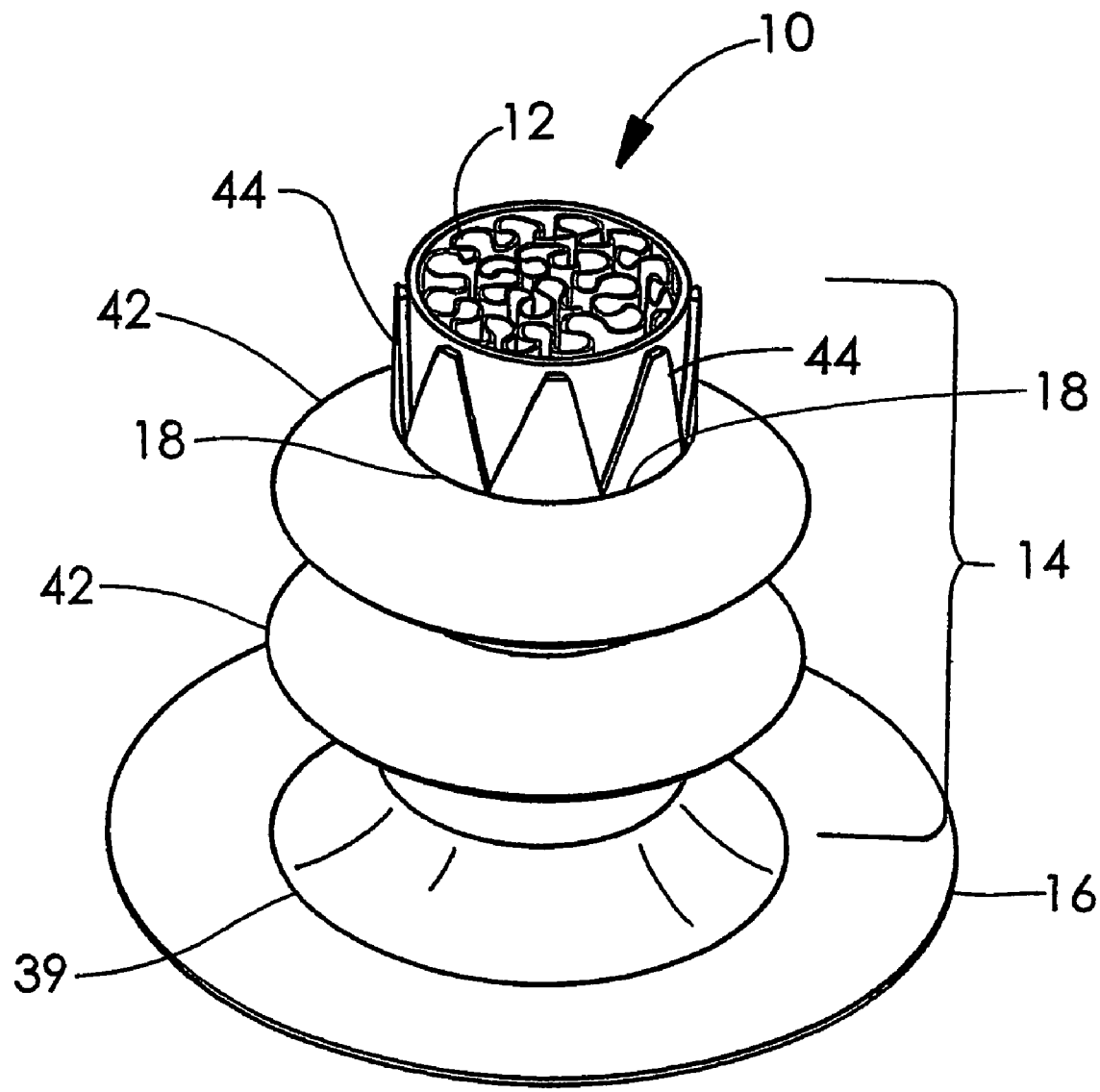
FIG. 4 is a perspective view of a hernia plug incorporating a barb component around the circumference of the plug.

FIG. 4 shows a perspective view of a plug 14 provided with a band 18 that includes one or more barbs 42, intended to aid in the securement or anchoring of plug 14 within a tissue defect. Additionally, barbs 42 may serve as the band component 18 that holds hollow members 12 together in a bundle. These barb components 42 may be made in a variety of ways. FIG. 4 shows two barbs made from discs of bioabsorbable material and provided with flanges 44 that enable the attachment of barbs 42 to the outer surface of plug 14. These anchoring barbs 42 may also be made by providing transverse corrugations 38 to corrugated sheet 32 prior to rolling corrugated sheet 32 to form plug 14, as described previously and shown in FIGS. 2A and 2B.

The preferred bioabsorbable material for making the present invention is in the form of a web of continuous filaments which are made of at least one semi-crystalline polymeric component covalently bonded as a linear block copolymer with or blended with one or more semi-crystalline or amorphous polymeric components. The filaments are intermingled together to form a porous web of filaments, the filaments having multiple contact points with each other within the web. The filaments are bonded at the contact points without requisite for added adhesive binders, adjuncts or post extrusion melt processing. The web may be provided in forms with relatively high cohesive shear strength. The polymeric components of the filaments exist, at least temporarily, in a homogenous substantially phase miscible uncrystallized state. If preserved in the homogenous substantially phase miscible uncrystallized state, the object can then be manipulated into a distinct desirable molded shape and then subsequently set or crystallized to retain the desired form particularly suitable for a specific use or application. Such a web is referred to herein as a "self-cohering," "self-bonding," or "autogenous-bonding" web. Accordingly, a self-cohering web has the ability of a melt formed structure, or component thereof, to effectively self-generate an attachment to itself without the requirement to undergo a melt, or undergo the requisite addition of supplementary adhesives, binders, or adhesive adjuncts either before or after structure formation.

Figure 5:
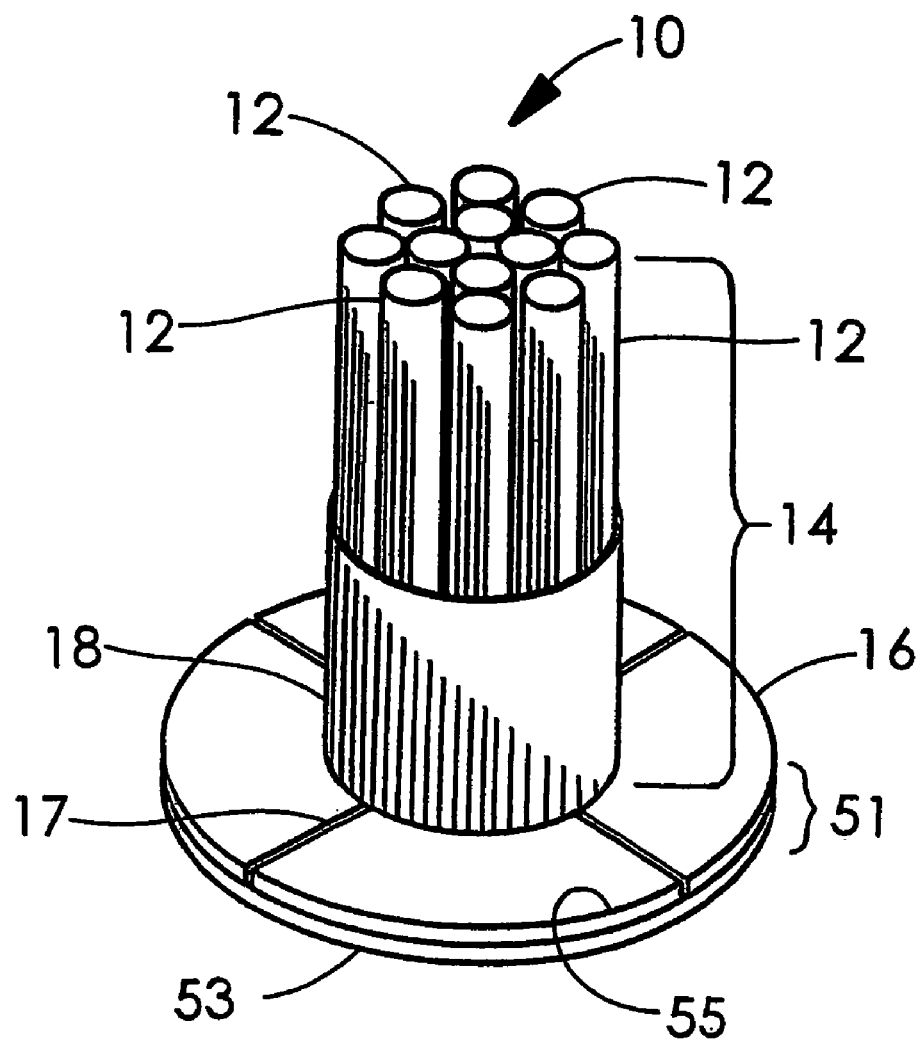
FIG. 5 is a perspective view of an embodiment of the hernia repair device incorporating a layered sheet component

FIG. 5 shows a perspective view of an alternative embodiment wherein sheet 16 is provided in two or more layers which may optionally be attached (e.g., laminated) together to create a composite sheet material 51 wherein the two layers have different properties. In a preferred embodiment, composite sheet material 51 includes a non-bioabsorbable layer 53 and a bioabsorbable layer 55. In use, bioabsorbable layer 55 is placed in contact with the tissue adjacent the defect. The non-bioabsorbable layer 53 is preferably ePTFE and the bioabsorbable layer 55 is preferably a PGA:TMC material in the form of a self-cohering web as taught by the Hayes patents referred to above and incorporated herein by reference.

Figure 5A:
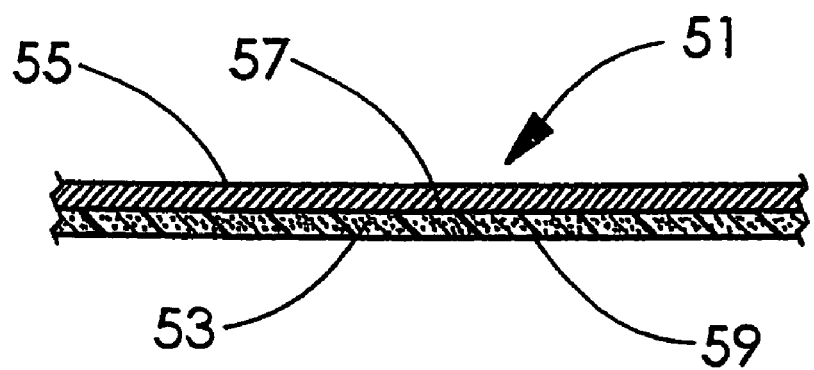
FIG. 5A shows a cross-section of a composite sheet material for use with the hernia repair device.

FIG. 5A shows a cross section of an alternative composite sheet material 51 wherein the non-bioabsorbable layer 53 has opposing surfaces 57 and 59 with different characteristics, for example, surface 57 being rougher and/or more open than surface 59. Rougher surface 57 is intended to encourage long term tissue attachment and ingrowth while smoother surface 59 is intended as a barrier to tissue attachment and ingrowth in order to prevent or reduce the likelihood of tissue adhesions. If layer 53 is a porous material, then smoother surface 59 may be provided with a suitably small pore size while rougher surface 57 may be provided with a suitably larger pore size. If desired, sheet 16 may be the result of attaching two different layers together (as by bonding with an adhesive or melt bonding, or by mechanical fastening means such as sewing) to achieve the desired different surface characteristics. Rougher surface 57 is preferably provided with a covering or coating of bioabsorbable layer 55; when this layer 55 is bioabsorbed after a suitable time, rougher surface 57 remains to provide the desired long term tissue attachment. The presence of the bioabsorbable layer 55 is anticipated to enhance healing as a result of the increased inflammatory tissue response to the bioabsorbable material. This may be desirable due to the chemically inert character of the PTFE material (which consequently does little to elicit a biological reaction from adjacent tissue when implanted by itself).

It is also apparent that the bioabsorbable layer 55 may be provided on one surface of an ePTFE material having similar opposing surfaces, as well as providing such a bioabsorbable layer on one surface of a differentially-sided ePTFE material.

A preferred material for the non-bioabsorbable layer 53 is GORE DUALMESH® Biomaterial with Corduroy™ surface (Flagstaff Ariz); this material has opposing surfaces with different tissue attachment and ingrowth characteristics as described above.

Figure 5B:
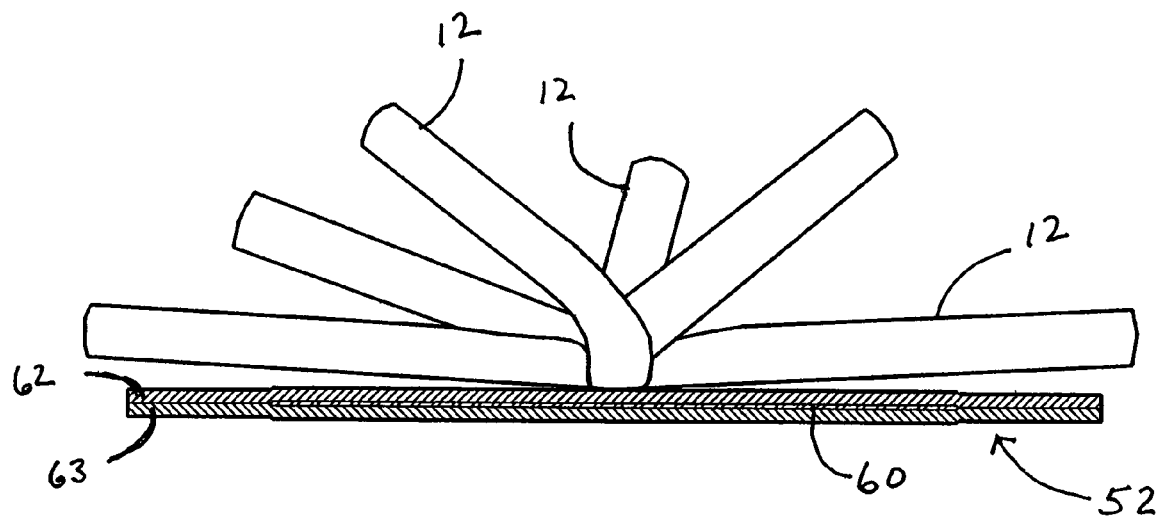
FIG. 5B shows a cross-section of a composite sheet material for use with the hernia repair device.
Figure 5C:
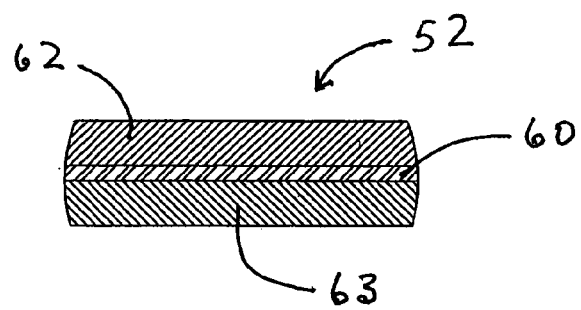
FIG. 5C shows a cross-section of a composite sheet material for use with the hernia repair device.

FIG. 5B shows a cross-section of a sheet material 16 of the present invention in the preferred form of a composite sheet material 52 wherein non-bioabsorbable material 60 is placed within bioabsorbable materials 62 and 63. FIG. 5C shows a cross-section of a sheet material 16 of the present invention in the preferred form of a composite sheet material 52 wherein non-bioabsorbable material 60 is placed between bioabsorbable materials 62 and 63. Either of these composite sheet materials can serve as preferred base member components of the present invention.

In both embodiments shown in FIGS. 5B and 5C, non-bioabsorbable material 60 is preferably a porous, expanded, polytetrafluoroethylene material (ePTFE). More preferably, the ePTFE material has one or more holes traversing the thickness of the material that are visible to the naked eye. The holes provide for ingrowth of tissue and additional flexibility of the composite sheet material. Most preferably, these "macroporous" ePTFE materials have holes arranged in a pattern that imparts additional flexibility to the composite sheet material while retaining sufficient mechanical strength to support damaged or injured tissue throughout the healing and rehabilitation process.

Figure 6:
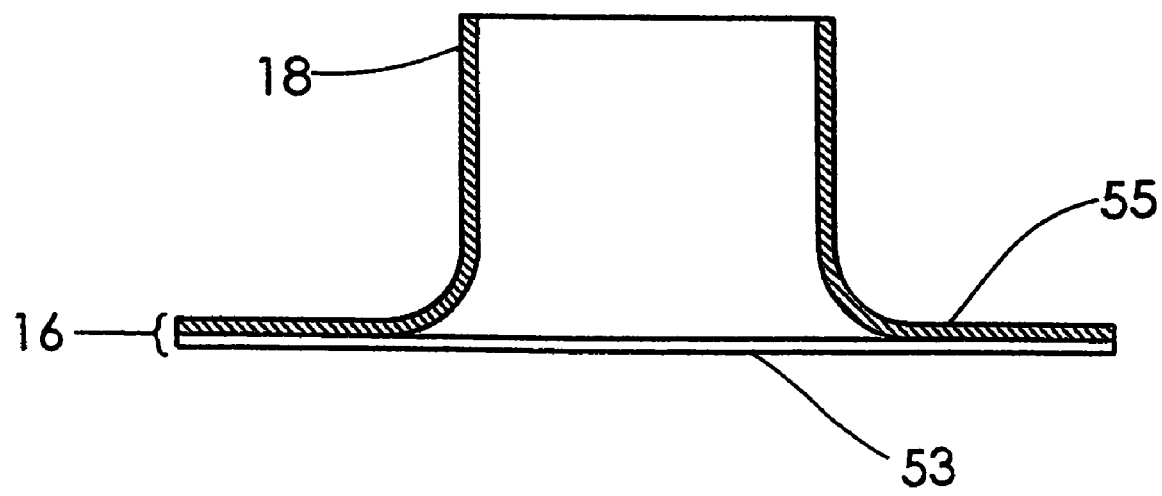
FIG. 6 is a longitudinal cross section that describes an alternative way to accomplish the attachment of the plurality of hollow members to the sheet component.

FIG. 6 is a longitudinal cross section of a band 18 that has been flared using suitable tooling to create the bioabsorbable layer 55 that may be adhered to a non-bioabsorbable layer 53 such as ePTFE. This describes an alternative way to accomplish the attachment of the plurality of hollow members to the sheet component.

The following examples are provided for illustrative purposes only as examples of particular embodiments of the described invention. As such, they are not intended to be limiting.

EXAMPLES

Example 1

This example describes the construction of a multiple tube hernia repair device of the present invention as shown in FIG. 1. A triblock copolymer of 67%/33% PGA:TMC (w/w) was acquired from US Surgical (Norwalk Conn.) and formed into a self-cohering web as generally taught by Hayes in U.S. Pat. No. 6,165,217. Sheets of this copolymer web material were formed into the 3 component types used in the construction of this device.

A first component used for making this device was a tube formed from the self-cohering web sheets that had an area density of approximately 8-10 mg/cm$^2$ and a thickness of approximately 0.3 mm. The first step in making a tube was to cut an approximately 25 mm wide strip of the self-cohering web material from a piece of "unset" web sheet perpendicular to the belt direction used in forming the web. This strip of "unset" web material was then wrapped lengthwise around an approximately 5 mm diameter stainless steel rod into a "cigarette roll" having an exposed edge at the surface of the resulting tube extending along the length of the tube. This material then self-cohered (as generally taught by Hayes in U.S. Pat. No. 6,165,217) at the overlapping portion of the "cigarette roll" to form a 5 mm diameter tube that was approximately 150 mm long. The strip of "unset" web material wrapped around the stainless steel rod was then placed into a Baxter Scientific Products (McGaw Park Ill.) constant temperature oven, model DK-43, for approximately 30 minutes at 75° C. to "set" the web. The stainless steel rod and "set" web material were then removed from the oven and allowed to cool. After cooling, the tube formed from the now "set" web material was slipped off of the stainless steel rod. Both ends of the "set" web tube were then trimmed leaving a tube that was approximately 90 mm long. Each tube was then placed onto a cutting die to create the notches 24 shown in FIG. 1B. A piece of 0.05 mm thick Mylar® sheet (DuPont Company, Wilmington Del.) was placed over the tube to protect it from contamination. A lightweight plastic-faced mallet was then used to lightly tap onto the tube through the Mylar® sheet to cut out two notches 24 and centering hole 26 with the cutting die. Multiple tubes were made using these methods.

Another component used in making this device was a disc-shaped planar sheet of approximately 38 mm in diameter. This disc-shaped planar sheet was made by first taking two 50 mm square sheets of the "unset" self-cohering web material, each with an area density of approximately 19 mg/cm$^2$ and approximately 1 mm thick. The two sheets were then stacked and placed in a restraining frame fitted about the perimeter of the stacked sheets. The restrained web material was then put into the Baxter Scientific Products constant temperature oven for approximately 30 minutes at 75° C. to bond the two pieces together to create a thicker sheet and to "set" the web. After letting the web material cool to room temperature, a disc was cut using an approximately 38 mm diameter circular cutting die punch.

A third component used in making this device was a band formed from an approximately 19 mm wide strip of copolymer web material. This copolymer web strip had an area density of approximately 6-8 mg/cm$^2$ and a thickness of approximately 0.3 mm. This was made by rolling the strip of "unset" self-cohering web material into a tube and then holding the overlapped ends together to allow for self-cohering. The unset web material was then put into a Baxter Scientific Products constant temperature oven for approximately 30 minutes at 75° C. The resulting band was approximately 19 mm in diameter.

The device was then assembled by taking the disc first and centering it on a centering pin extending from the center of the surface of an assembly fixture. Then six of the tubes with notches and centering holes were placed on top of the disc, also centering them on the centering pin. The tubes were arranged so that they were equally spaced radially. The assembly was then placed onto a Branson model 8400 ultrasonic welder (Branson Sonic Power Co., Danbury Conn.). The ultrasonic welder had a Branson catenoidal horn, model 609-010-020 and an approximately 7.6 mm diameter tip that had an approximately 3.2 mm hole in the center to accommodate the centering pin of the assembly fixture. The ultrasonic welder also had a 1:0.6 booster. The downstop was set at approximately 0.4 mm with the downspeed set at number 4. Pressure was set at approximately 0.08 MPa with the trigger set at number 2; time was set to 0.2 seconds and the hold duration set at 1.0 seconds.

The ultrasonic welder was shut and activated 3 times for each device. After ultrasonic welding, the six tubes were securely attached to the disc-shaped sheet. The tubes were then folded up so that they were oriented to be substantially perpendicular to the sheet component. The band component was then placed around the tubes to hold them in a bundled configuration wherein the tubes were substantially parallel to each other along their lengths. Four slits, spaced equally apart, were then cut into the disc approximately three quarters of the way from the perimeter of the disc to the center to facilitate insertion on the device into a hernia defect site.

Example 2

This example describes the construction of a corrugated tube hernia repair device of the present invention as shown in FIG. 4. A triblock copolymer of 50% PGA:TMC (w/w) was made and formed into a self-cohering web as generally taught by Hayes in U.S. Pat. No. 6,165,217. Sheets of this copolymer web material were formed into some of the components used in the construction of this device. Other components were made from expanded polytetrafluoroethylene (ePTFE) and from a bioabsorbable polymer adhesive, as described below.

A corrugated sheet was made by first placing a piece of the "unset" PGA:TMC web sheet (approximately 100 mm square, about 0.2 mm thick having and having an area density of approximately 4-6 gm/cm$^2$) onto a piece of PeCap® polyester screen, product number 7-1000/45 (Sefar America, Monterey Park Calif.) material. This screen material, by virtue of its surface texture, was used to restrain the web material from dimensional change during the "setting" process. A fixture approximately 125 mm square was then placed onto the surface of the web sheet. The fixture was provided with a set of multiple parallel rods with all of their centerlines in the same plane, the rods being of approximately 2.4 mm diameter and spaced 5.3 mm center-to-center. These rods acted as mandrels for forming the hollow members of the corrugation.

A second piece of "unset" web material of the same type as the first and of approximately the same dimensions was then placed on top of the multiple parallel rod fixture. Unsecured rods of approximately the same diameter as the rods in the fixture were then placed on top of the second piece of "unset" web material, between the parallel rods of the underlying fixture. These unsecured rods were individually pushed down until they were in the same plane as the parallel rods of the underlying fixture. The result was that the second piece of "unset" web material now formed the hollow members of the corrugated sheet as it assumed a convoluted shape with self-cohering contact points on the bottom piece of "unset" web material. Another piece of PeCap® polyester screen was placed on top of the upper piece of "unset" web material to restrain it from dimensional changes during the "setting" process. An aluminum plate was placed on top of the polyester and then a weight was placed on top of the entire assembly.

The assembly was then placed into an oven at 80° C. for 30 minutes to "set" the web material. After "setting" in the oven, the web material was allowed to cool and then removed from the fixture of multiple parallel rods.

Another component used in making this device was a sheet component with a fillet and band for accepting a rolled up piece of corrugated web material. The first step in making this sheet component was to provide a piece of "unset" web sheet material approximately 50 mm square. A circular cutting die was used to cut an approximately 13 mm diameter hole in the center of it. A 19 mm diameter aluminum rod, approximately 150 mm long, was then fixtured to stand perpendicularly on a flat aluminum plate. The piece of "unset" web material with a hole in its center was then pushed over the aluminum rod. Since the hole in the "unset" web was smaller than the diameter of the aluminum rod, and because the "unset" web material was deformable, the difference in diameters between the hole in the web material and the aluminum rod produced a flared hole in the "unset" web. The aluminum rod and web material were then placed into an oven at 80° C. for 30 minutes to "set" the web material. After allowing the web material to cool, it was removed from the aluminum rod. The flared hole in the "set" web material formed a combined fillet and band (as in FIG. 6) for accepting the corrugated web material. The piece of "set" web material with the flange was then adhered to a piece of ePTFE material by using a bioabsorbable adhesive. The adhesive was made from a mixture of poly(85% d,l-lactide-co-15% glycolide) (by mole; abbreviated as 85% d,l-PLA:15% PGA) mixed 1:4 by weight in acetone. It is apparent that this device could be made without the ePTFE layer.

Barb components (FIG. 4, reference no. 42) were individually formed by taking a piece of "unset" PGA:TMC web material approximately 65 mm long×13 mm wide and wrapping this lengthwise around a suitably tapered mandrel chosen to shape the downwardly-angled barb. The strip of "unset" web material was temporarily restrained to the mandrel by using a piece of PTFE pipe tape. The tapered mandrel and restrained "unset" web material were then put into an oven at approximately 80° C. for approximately 30 minutes to "set" the web material. After the web material was "set" in the oven, it was removed from the mandrel. Cutouts were then made to the center region of the now tapered band to create flanges 44. The device was then assembled by taking the corrugated sheet and rolling it into a tube. Some of the bioabsorbable adhesive was applied to the circumference of one end of this tube and also to the walls of the filleted band portion to be attached to the sheet component. The end of the tube with adhesive on it was then inserted in a perpendicular orientation into the filleted band portion of the sheet component. Bioabsorbable adhesive was then applied to the interiors of a pair of anchoring barbs, after which they were immediately fitted over the circumference of the plug component.

Example 3

This example describes a method used to alter the stiffness and rate of bioabsorption of a bioabsorbable device. A solution was made by mixing 65% d,l-PLA:35% PGA available from Birmingham Polymers (Birmingham Ala.) in a 1:10 ratio by weight with acetone. A device as described in Example 1 was dipped into this solution which imbibed into the structure of the device, and then allowed to air dry. The resulting coated device was stiffer than prior to imbibing. Alternatively, this solution could be sprayed onto devices to achieve similar effects. Other copolymer ratios can also be used to vary the stiffness and rate of bioabsorption. Also, other ratios of polymer:acetone can be used to vary the final amount of polymer imbibed into or sprayed onto the structure of the device.

Example 4

This example describes construction of a preferred embodiment of the present invention having a base member in the form of a composite sheet material having a non-bioabsorbable component placed within a bioabsorbable component. This composite base member can be used with any of the embodiments described herein.

The composite sheet material for use as the base member of the present invention was made in the form of a laminate of a non-bioabsorbable ePTFE material and a bioasborbable PGA:TMC self-cohering web material (67:33 weight percent) as taught by Hayes (Ibid.). The ePTFE material made according to U.S. Pat. No. 5,858,505, which is incorporated herein by reference, was obtained from W. L. Gore & Associates, Inc., Flagstaff, Ariz. under the tradename GORE MYCROMESH® Biomaterial. In addition to having a plethora of interconnected microscopic sized pores coursing throughout the body of the ePTFE material, the material has holes traversing the thickness of the material visible to the naked eye. The starting materials for the bioabsorbable PGA:TMC component were obtained as described above in Example 1.

The composite material was constructed by centering a circular 7 cm diameter piece of ePTFE material between two 10 cm×10 cm sheets of PGA:TMC material. The PGA:TMC material was in the form of an unset web having an area density between 20 mg/cm$^2$ and 25 mg/cm$^2$. The composite was overlaid on both sides with a woven polyester web material (SEFAR AMERICA, INC, SEFAR product number 7-1000/45 PeCap® polyester endless belt) and placed in a restraining apparatus. Approximately five (5) pounds of force was applied to the polyester web pieces with the apparatus.

The restrained combination was placed in a constant temperature oven at 100° C. for ten (10) minutes in order to set the bioabsorbable PGA:TMC web material and enclose the non-bioabsorbable ePTFE material within the bioabsorbable material. The composite material was allowed to cool to room temperature before being removed from the restraining apparatus.

Excess bioabsorbable material was trimmed from the composite sheet material to form a base member of the present invention. The base member was attached to a plurality of substantially hollow members as described in Example 1.

Example 5

This example describes construction of a preferred embodiment of the present invention having a base member in the form of a composite sheet material having a non-bioabsorbable component placed between layers of bioabsorbable material. In this example, the bioabsorbable self-cohering web had a volume percent of 67:33, an area density of approximately 50 mg/cm$^2$, and a volume density of 0.35 g/cc. The ePTFE material was obtained from W. L. Gore & Associates, Inc., Flagstaff, Ariz. under the tradename GORE DUALMESH® Biomaterial. The ePTFE material is in the form of a sheet having different textures on opposite sides of the sheet material to elicit different tissue responses at an implantation site.

In this example, the non-bioabsorbable ePTFE material was placed between two layers of bioabsorbable PGA:TMC material, restrained as described in Example 4, and ultrasonically welded together.

The ultrasonic welder had a Branson circular high gain horn, model 318 004 145 with an approximately 5 cm diameter tip having a machined face honeycomb hole pattern. Each 6 mm hexagon machined hole in the honeycomb pattern was spaced at 1 mm. The ultrasonic welder also had a 1:2.5 booster. The downspeed was set at number 4. Applied pressure was set at approximately 0.65 MPa with the trigger set at number 2. The welding time was 0.8 seconds and assembly held in place for a duration of 2.5 seconds.

Excess bioabsorbable material was trimmed from the composite sheet material to form a base member of the present invention. The base member was attached to a plurality of substantially hollow members as described in Example 1.

While the principles of the invention have been made clear in the illustrative embodiments set forth herein, it will be obvious to those skilled in the art to make various modifications to the structure, arrangement, proportion, elements, materials and components used in the practice of the invention. To the extent that these various modifications do not depart from the spirit and scope of the appended claims, they are intended to be encompassed therein.

The invention claimed is:

1. An implantable tissue repair device comprising:
   a plurality of discrete tubes each having a length;
   wherein each discrete tube has two ends and at least one of said ends is open;
   wherein each discrete tube is made of a bioabsorbable polymeric material;
   wherein each discrete tube is attached to a substantially planar base member at a fold along a mid-point of said discrete tube; and
   wherein said substantially planar base member is a composite of a non-bioabsorbable polymeric material placed within a bioabsorbable polymeric material in the form of a self-cohering web.

2. The implantable tissue repair device of claim 1 wherein said self-cohering web includes a co-polymer of polyglycolic acid and trimethylene carbonate (PGA:TMC).

3. The implantable tissue repair device of 1 wherein said non-bioabsorbable polymeric includes porous expanded polytetrafluoroethylene (ePTFE).

4. An implantable tissue repair device comprising:
   a plurality of discrete tubes each having a length;
   wherein each discrete tube has two ends and at least one of said ends is open;
   wherein each discrete tube is made of a bioabsorbable polymeric material;
   wherein each discrete tube is attached to a substantially planar base member at a fold along a mid-point of said discrete tube; and
   wherein said substantially planar base member is a composite of a non-bioabsorbable polymeric material placed between at least two layers of a bioabsorbable polymeric material in the form of a self-cohering web.

5. The implantable tissue repair device of claim 4 wherein said self-cohering web includes a co-polymer of polyglycolic acid and trimethylene carbonate (PGA:TMC).

6. The implantable tissue repair device of 4 wherein said non-bioabsorbable polymeric includes porous expanded polytetrafluoroethylene (ePTFE).

* * * * *